(12) United States Patent
Brandl et al.

(10) Patent No.: US 7,807,714 B2
(45) Date of Patent: Oct. 5, 2010

(54) FUNGICIDAL COMPOSITIONS

(75) Inventors: Franz Brandl, Basel (CH); Michael Oostendorp, Basel (CH); Ronald Zeun, Stein (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 12/278,731

(22) PCT Filed: Feb. 7, 2007

(86) PCT No.: PCT/EP2007/001034

§ 371 (c)(1),
(2), (4) Date: Nov. 24, 2008

(87) PCT Pub. No.: WO2007/090623

PCT Pub. Date: Aug. 16, 2007

(65) Prior Publication Data

US 2009/0318505 A1 Dec. 24, 2009

(30) Foreign Application Priority Data

Feb. 9, 2006 (EP) .................................. 06002628

(51) Int. Cl.
*A01N 37/10* (2006.01)
*A01N 43/36* (2006.01)
(52) U.S. Cl. .................... 514/533; 514/229.2; 514/341; 514/405; 514/422; 514/616

(58) Field of Classification Search ................. 514/341, 514/405, 422, 616
See application file for complete search history.

(56) References Cited

FOREIGN PATENT DOCUMENTS

| WO | 03/074491 A | 9/2003 |
|---|---|---|
| WO | 2005/034628 A | 4/2005 |
| WO | 2005/041653 A | 5/2005 |
| WO | 2006/015866 A | 2/2006 |
| WO | 2006/032356 A | 3/2006 |

*Primary Examiner*—Raymond J Henley, III
(74) *Attorney, Agent, or Firm*—William F. Mulholland, II

(57) ABSTRACT

A composition suitable for control of diseases caused by phytopathogens comprising (A) a compound of formula (I) or a tautomer of such a compound; and component (B) and component (C) are pesticides as described in claim 1.

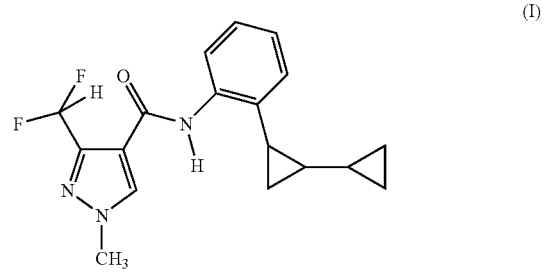

18 Claims, No Drawings

FUNGICIDAL COMPOSITIONS

This application is a National Stage Entry under 35 USC §371 of International application serial number PCT/EP2007/001034, filed on Feb. 7, 2007, which claims priority to EP 06002628.3, filed on Feb. 9, 2006, the contents of which are incorporated herein by reference.

The present invention relates to novel fungicidal compositions suitable for control of diseases caused by phytopathogens, especially phytopathogenic fungi, to a method of controlling diseases on useful plants and to a method of protecting storage goods.

It is known that certain o-cyclopropyl-carboxanilide derivatives have biological activity against phytopathogenic fungi, e.g. known from WO 03/74491. On the other hand various fungicidal compounds of different chemical classes and some mixtures thereof are widely known as plant fungicides for application in various crops of cultivated plants. However, crop tolerance and activity against phytopathogenic fungi do not always satisfy the needs of agricultural practice in many incidents and aspects.

Out of the above-mentioned needs of agricultural practice for increased crop tolerance and/or increased activity against phytopathogenic fungi, there is therefore proposed in accordance with the present invention a novel composition suitable for control of diseases caused by phytopathogens comprising (A) a compound of formula I

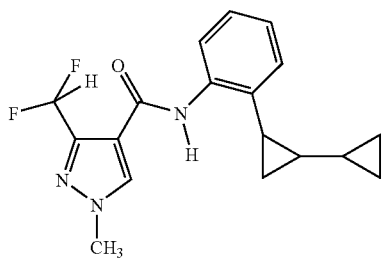

or a tautomer of such a compound;

(B) a fungicide selected from the group consisting of fludioxonil (368), metalaxyl (516), mefenoxam (517), cyprodinil (208), azoxystrobin (47), tebuconazole (761), difenoconazole (247) and thiabendazole (790); and (C) a compound selected from the group consisting of an azole fungicide; an anilino-pyrimidine fungicide; a strobilurin fungicide; an acylalanine fungicide; a benzimidazole fungicide; a fungicide selected from the group consisting of silthiofam (729), furametpyr (411) and penthiopyrad; and an insecticide selected from the group consisting of abamectin (1), clothianidin (165), cyromazine (209), diafenthiuron (226), diazinon (227), emamectin benzoate (291), fenoxycarb (340), fosthiazate (408), imidacloprid (458), lambda-cyhalothrin (198), lufenuron (490), methidathion (529), methiocarb (530), profenofos (662), pymetrozine (688), spinosad (737), tefluthrin (769), thiamethoxam (792), thiodicarb (799), a compound of formula C-1

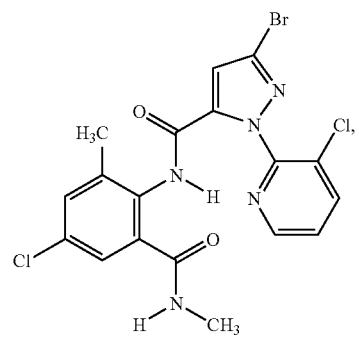

and a compound of formula C-2

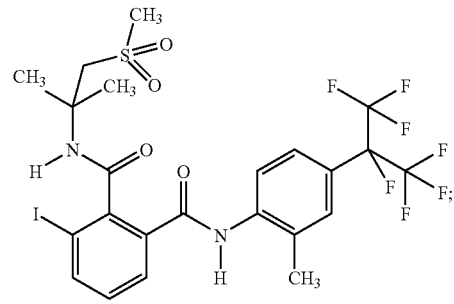

wherein (B) and (C) are different compounds.

It has been found that the use of component (B) and component (C) in combination with component (A) surprisingly and substantially enhance the effectiveness of the latter against fungi, and vice versa. Additionally, the method of the invention is effective against a wider spectrum of such fungi that can be combated with the active ingredients of this method, when used solely.

A further aspect of the present invention is a method of controlling diseases on useful plants or on propagation material thereof caused by phytopathogens, which comprises applying to the useful plants, the locus thereof or propagation material thereof a composition according to the invention.

Preferred is a method of controlling diseases on useful plants or on propagation material thereof caused by phytopathogens, which comprises applying to the propagation material of the useful plants a composition according to the invention.

The compounds of formula I and their manufacturing processes starting from known and commercially available compounds are described in WO 03/074491. The compound of formula I has two chiral centers (highlighted by asterics):

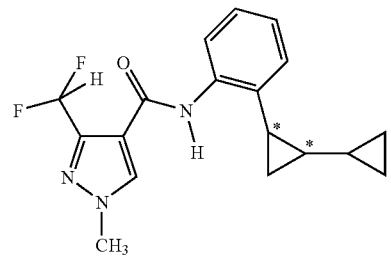

and occurs in four different stereoisomers: two trans-isomers and two cis-isomers ("trans" and "cis" are used to characterize the stereochemistry at the cyclopropyl ring which is directly attached to the phenyl moiety). The invention covers compositions comprising all such stereoisomers and mixtures thereof in any ratio.

A preferred embodiment of the present invention is represented by those compositions which comprise as component A) the trans-isomer of the compound of formula I, preferably in racemic form. A further preferred embodiment of the present invention is represented by those compositions which comprise as component A) the cis-isomer of the compound of formula I, preferably in racemic form. A further preferred embodiment of the present invention is represented by those compositions which comprise as component A) mixture of racemic trans-isomers and racemic cis-isomers, in a trans/cis-ratio of from 1:1 to 100:1, for example 1:1, 2:1, 3:1, 4:1, 5:1, 6:1, 7:1, 8:1, 9:1, 10:1, 20:1, 50:1 or 100:1. Further preference is given to ratios from 2:1 to 100:1, even more preferably 4:1 to 10:1.

The components (B) and the components (C) are known. Where the components (B) and the components (C) are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular component (B) or component (C); for example, the compound "abamectin" is described under entry number (1). Most of the components (B) and components (C) are referred to hereinabove by a so-called "common name". The following components (C) are registered under a CAS-Reg. No.: Penthiopyrad (CAS 183675-82-3); Orysastrobin (CAS 248593-16-0). The compound of formula B-1 is described in EP-0-936-213 and is also known as Enestrobin. The compound of formula C-1 is described in WO-03/015519. The compound of formula C-2 is described in EP-1-006-107-A2, registered under CAS-272451-65-7 and is also known as Flubendiamide.

Examples of especially suitable compounds as component (C) are compounds selected from the following group P:

Group P: Especially Suitable Compounds as Component (C) in the Compositions According to the Invention:

an azole fungicide selected from the group consisting of azaconazole (40), bromuconazole (96), cyproconazole (207), difenoconazole (247), diniconazole (267), diniconazole-M (267), epoxiconazole (298), fenbuconazole (329), fluquinconazole (385), flusilazole (393), flutriafol (397), hexaconazole (435), imazalil (449), imibenconazole (457), ipconazole (468), metconazole (525), myclobutanil (564), oxpoconazole (607), pefurazoate (618), penconazole (619), prochloraz (659), propiconazole (675), prothioconazole (685), simeconazole (731), tebuconazole (761), tetraconazole (778), triadimefon (814), triadimenol (815), triflumizole (834) triticonazole (842), diclobutrazol (1068), etaconazole (1129), furconazole (1198), furconazole-cis (1199) and quinconazole (1378);

an anilino-pyrimidine fungicide selected from the group consisting of cyprodinil (208), mepanipyrim (508) and pyrimethanil (705);

a strobilurin fungicide selected from the group consisting of azoxystrobin (47), dimoxystrobin (226), fluoxastrobin (382), kresoxim-methyl (485), metominostrobin (551), orysastrobin, picoxystrobin (647), pyraclostrobin (690); trifloxystrobin (832) and a compound of formula B-1

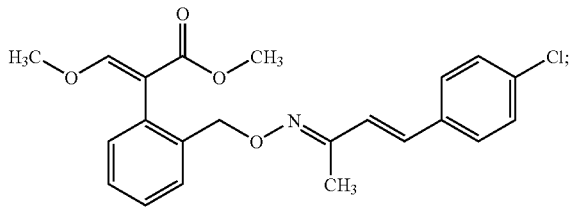

an acylalanine fungicide selected from the group consisting of benalaxyl (56); benalaxyl-R; furalaxyl (410); metalaxyl (516) and mefenoxam (Metalaxyl-M) (517);

a benzimidazole fungicide selected from the group consisting of benomyl (62); carbendazim (116); fuberidazole (419) and thiabendazole (790);

a fungicide selected from the group consisting of silthiofam, furametpyr and penthiopyrad; and an insecticide selected from the group consisting of abamectin; clothianidin; cyromazine; diafenthiuron; diazinon; emamectin benzoate; fenoxycarb; fosthiazate; imidacloprid; lambda-cyhalothrin; lufenuron; methidathion; methiocarb; profenofos; pymetrozine; spinosad; tefluthrin; thiamethoxam; thiodicarb; a compound of formula C-1 and a compound of formula C-2.

The following compositions are preferred:

A composition comprising (A) a compound of the formula (I), (B) fludioxonil and (C) one compound selected from the group P.

A composition comprising (A) a compound of the formula (I), (B) metalaxyl and (C) one compound selected from the group P.

A composition comprising (A) a compound of the formula (I), (B) mefenoxam and (C) one compound selected from the group P.

A composition comprising (A) a compound of the formula (I), (B) cyprodinil and (C) one compound selected from the group P.

A composition comprising (A) a compound of the formula (I), (B) azoxystrobin and (C) one compound selected from the group P.

A composition comprising (A) a compound of the formula (I), (B) tebuconazole and (C) one compound selected from the group P.

A composition comprising (A) a compound of the formula (I), (B) difenoconazole and (C) one compound selected from the group P.

A composition comprising (A) a compound of the formula (I), (B) thiabendazole and (C) one compound selected from the group P.

An example of such a preferred composition is a composition comprising (A) a compound of the formula (I), (B) fludioxonil and (C) the first compound selected from the group P, which is the compound azaconazole.

Further preferred are compositions which comprise as component (B) fludioxonil and as component (C) an azole fungicide, a strobilurin fungicide, an acylalanine fungicide or a benzimidazole fungicide. Within said compositions, preferred component (C) is difenoconazole, mefenoxam or thiamethoxam; even more preferably difenoconazole or mefenoxam.

Further preferred are compositions which comprise as component (B) mefenoxam or metalaxyl and as component (C) an azole fungicide, a strobilurin fungicide, an acylalanine fungicide or a benzimidazole fungicide. Within said compositions, preferred component (C) is difenoconazole, azoxystrobin, tebuconazole or thiabendazole; even more preferably difenoconazole or tebuconazole.

A further embodiment of the invention is represented by those mixtures which comprise as component (B) cyprodinil, azoxystrobin, tebuconazole, difenoconazole or thiabendazole.

Throughout this document the expression "composition" stands for the various mixtures or combinations of component (A), component (B) and component (C), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying component (A), component (B) and component (C) is not essential for working the present invention.

The compositions according to the invention may also comprise one or more additional pesticides. An example for such a composition according to the invention is a composition comprising a compound of formula I, fludioxonil, mefenoxam and cyprodinil, or a composition comprising a compound of formula I, fludioxonil, mefenoxam, cyprodinil and thiamethoxam, or a composition comprising a compound of formula I, fludioxonil, mefenoxam and difenoconazole, or a composition comprising a compound of formula I, fludioxonil, mefenoxam and azoxystrobin, or a composition comprising a compound of formula I, fludioxonil, mefenoxam, azoxystrobin and thiabendazole, or a composition comprising a compound of formula I, fludioxonil, mefenoxam and thiabendazole, or a composition comprising a compound of formula I, fludioxonil, mefenoxam and thiamethoxam, or a composition comprising a compound of formula I, fludioxonil, mefenoxam and tefluthrin, or a composition comprising a compound of formula I, fludioxonil, difenoconazole and thiamethoxam, or a composition comprising a compound of formula I, fludioxonil, difenoconazole and tefluthrin, or a composition comprising a compound of formula I, mefenoxam, thiabendazole and azoxystrobin, or a composition comprising a compound of formula I, mefenoxam, difenoconazole and thiamethoxam, or a composition comprising a compound of formula I, mefenoxam, thiabendazole and thiamethoxam, or a composition comprising a compound of formula I, mefenoxam, difenoconazole and tefluthrin, or a composition comprising a compound of formula I, mefenoxam, thiabendazole and tefluthrin.

The compositions according to the invention are effective against harmful microorganisms, such phytopathogenic fungi and bacteria; preferably the microorganisms are phytopathogenic fungi.

The active ingredient combinations are effective especially against phytopathogenic fungi belonging to the following classes: Ascomycetes (e.g. *Venturia, Podosphaera, Erysiphe, Monilinia, Mycosphaerella, Uncinula*); Basidiomycetes (e.g. the genus *Hemileia, Rhizoctonia, Puccinia, Ustilago, Tilletia*); Fungi imperfecti (also known as Deuteromycetes; e.g. *Botrytis, Helminthosporium, Rhynchosporium, Fusarium, Septoria, Cercospora, Alternaria, Pyricularia* and *Pseudocercosporella herpotrichoides*); Oomycetes (e.g. *Phytophthora, Peronospora, Pseudoperonospora, Albugo, Bremia, Pythium, Pseudosclerospora, Plasmopara*).

According to the invention "useful plants" typically comprise the following species of plants: cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compositions of the present invention may also be used in the field of protecting storage goods against attack of fungi. According to the present invention, the term "storage goods" is understood to denote natural substances of vegetable and/or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The compositions according the present invention can prevent disadvantageous effects such as decay, discoloration or mold. Preferably "storage goods" is understood to denote natural substances of vegetable origin and/or their processed forms, more preferably fruits and their processed forms, such as pomes, stone fruits, soft fruits and citrus fruits and their processed forms. In another preferred embodiment of the invention "storage goods" is understood to denote wood.

Therefore a further aspect of the present invention is a method of protecting storage goods, which comprises applying to the storage goods a composition according to the invention.

The compositions of the present invention may also be used in the field of protecting technical material against attack of fungi. According to the present invention, the term "technical material" includes paper; carpets; constructions; cooling and heating systems; wall-boards; ventilation and air conditioning systems and the like; preferably "technical material" is understood to denote wall-boards. The compositions according the present invention can prevent disadvantageous effects such as decay, discoloration or mold.

The compositions according to the present invention are particularly effective against seedborne and soilborne diseases, such as downey mildews, *Alternaria* spp., *Ascochyta* spp., *Aspergillus* spp., *Penicillium* spp., *Botrytis cinerea, Cercospora* spp., *Claviceps purpurea, Cochliobolus sativus, Colletotrichum* spp., *Diplodia maydis, Epicoccum* spp., *Fusarium culmorum, Fusarium graminearum, Fusarium moniliforme, Fusarium oxysporum, Fusarium proliferatum, Fusarium solani, Fusarium subglutinans, Gäumannomyces graminis, Helminthosporium* spp., *Microdochium nivale, Phoma* spp., *Phytophthara* spp., *Plasmopara* spp., *Pyrenophora graminea, Pyricularia oryzae, Pythium* spp., *Rhizoctonia solani, Rhizoctonia cerealis, Sclerotinia* spp., *Septoria* spp., *Sphacelotheca reilliana, Thielaviopsis basicola, Tilletia* spp., *Typhula incarnata, Urocystis occulta, Ustilago* spp. or *Verticillium* spp. The compositions according to the present invention are in particular effective against pathogens of cereals, such as wheat, barley, rye or oats; maize; rice; cotton; soybean; turf; sugarbeet; oil seed rape; potatoes; pulse crops, such as peas, lentils or chickpea; and sunflower. The compositions according to the present invention are furthermore particularly effective against rusts; powdery mildews; leaf-spot species; early blights; molds and post harvest diseases; especially against *Puccinia* in cereals; *Phakopsora* in soybeans; *Hemileia* in coffee; *Phragmidium* in roses; *Alternaria* in potatoes, tomatoes and *cucurbits; Sclerotinia* in vegetables, sunflower and oil seed rape; black rot, red fire, powdery mildew, grey mold and dead arm disease in vine; *Botrytis cinerea* in fruits; *Monilinia* spp. in fruits and *Penicillium* spp. in fruits. The compositions of the present invention are of particular interest for controlling a large number of fungi in various useful plants or their seeds, especially in field crops such as potatoes, tobacco and sugarbeets, and wheat, rye, barley, oats, rice, maize, lawns, cotton, soybeans, oil seed rape, pulse crops, sunflower, coffee, sugarcane, fruit and ornamentals in horticulture and viticulture, in vegetables such as cucumbers, beans and *cucurbits.*

The compositions according to the invention are particularly useful for controlling the following plant diseases: *Alternaria* species in fruit and vegetables; *Ascochyta* species in pulse crops; *Botrytis cinerea* (gray mold) in strawberries, tomatoes, sunflower and grapes; *Cercospora arachidicola* in groundnuts; *Cochliobolus sativus* in cereals; *Colletotrichum* species in pulse crops; *Erysiphe cichoracearum* and *Sphaerotheca fuliginea* in *cucurbits; Erysiphe graminis* in cereals; *Fusarium graminearum* in cereals and maize; *Fusarium culmorum* in cereals; *Fusarium* spp. in cotton, soybean and potatoes; *Fusarium moniliforme* in maize; *Fusarium proliferatum* in maize; *Fusarium subglutinans* in maize; *Fusarium oxysporum* in maize; *Gäumannomyces graminis* in cereals and lawns; *Giberella fujikuroi* in rice; *Helminthosporium maydis* in maize; *Helminthosporium oryzae* in rice; *Helminthosporium solani* on potatoes; *Hemileia vastatrix* on coffee; *Microdochium rivale* in wheat and rye; *Mycosphaerella pinbides* in peas; *Phakopsora pachyrhizi* in soybean; *Puccinia* species in cereals; *Phragmidium mucronatum* in roses; *Phoma* spp. in sugarbeet; *Phoma exigua* in potatoes; *Pythium* spp. in cereals, cotton, maize and soybean; *Plasmopara halstedii* in sunflowers; *Pyrenophora graminea* in barley; *Pyricularia oryzae* in rice; *Rhizoctonia* species in cotton, soybean, cereals, maize, potatoes, rice and lawns; *Sclerotinia homeocarpa* in lawns; *Septoria* spp. in cereals; *Sphacelotheca reilliana* in maize; *Tilletia* species in cereals; *Typhula incarnata* in barley; *Uncinula necator, Guignardia bidwellii* and *Phomopsis viticola* in vines; *Urocystis occulta* in rye; *Ustilago* species in cereals and maize; *Monilinia fructicola* on stone fruits; *Monilinia fructigena* on fruits; *Monilinia laxa* on stone fruits; *Penicillium digitatum* on citrus; *Penicillium* expansum on apples; and *Penicillium italicum* on citrus.

The compositions according to the invention are preventively and/or curatively valuable active ingredients in the field of pest control, even at low rates of application, which have a very favorable biocidal spectrum and are well tolerated by warm-blooded species, fish and plants.

Some of the active ingredients according to the invention are known for their insecticidal action act against all or individual developmental stages of normally sensitive, but also resistant, animal pests, such as insects or representatives of the order Acarina. The insecticidal or acaricidal activity of compositions according to the invention, which comprise said active ingredients, can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:

from the order Acarina, for example,

*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;

from the order Anoplura, for example,

Haematopinus spp., Linognathus spp., Pediculus spp., Pemphigus spp. and Phylloxera spp.;

from the order Coleoptera, for example,

Agriotes spp., Anthonomus spp., Atomaria linearis, Chaetocnema tibialis, Cosmopolites spp., Curculio spp., Dermestes spp., Diabrotica spp., Epilachna spp., Eremnus spp., Leptinotarsa decemlineata, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.; from the order Diptera, for example, Aedes spp., Antherigona soccata, Bibio hortulanus, Calliphora erythrocephala, Ceratitis spp., Chrysomyia spp., Culex spp., Cuterebra spp., Dacus spp., Drosophila melanogaster, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., Oscinella frit, Pegomyia hyoscyami, Phorbia spp., Rhagoletis pomonella, Sciara spp., Stomoxys spp., Tabanus spp., Tannia spp. and Tipula spp.;

from the order Heteroptera, for example,

Cimex spp., Distantiella theobroma, Dysdercus spp., Euchistus spp., Eurygaster spp., Leptocorisa spp., Nezara spp., Piesma spp., Rhodnius spp., Sahlbergella singularis, Scotinophara spp. and Triatoma spp.;

from the order Homoptera, for example,

Aleurothrixus floccosus, Aleyrodes brassicae, Aonidiella spp., Aphididae, Aphis spp., Aspidiotus spp., Bemisia tabaci, Ceroplaster spp., Chrysomphalus aonidium, Chrysomphalus dictyospermi, Coccus hesperidum, Empoasca spp., Eriosoma larigerum, Erythroneura spp., Gascardia spp., Laodelphax spp., Lecanium corni, Lepidosaphes spp., Macrosiphus spp., Myzus spp., Nephotettix spp., Nilaparvata spp., Parlatoria spp., Pemphigus spp., Planococcus spp., Pseudaulacaspis spp., Pseudococcus spp., Psylla spp., Pulvinaria aethiopica, Quadraspidiotus spp., Rhopalosiphum spp., Saissetia spp., Scaphoideus spp., Schizaphis spp., Sitobion spp., Trialeurodes vaporariorum, Trioza erytreae and Unaspis citri;

from the order Hymenoptera, for example,

Acromyrmex, Atta spp., Cephus spp., Diprion spp., Diprionidae, Gilpinia polytoma, Hoplocampa spp., Lasius spp., Monomorium pharaonis, Neodiprion spp., Solenopsis spp. and Vespa spp.;

from the order Isoptera, for example,

Reticulitermes spp.;

from the order Lepidoptera, for example,

Acleris spp., Adoxophyes spp., Aegeria spp., Agrotis spp., Alabama argillaceae, Amylois spp., Anticarsia gemmatalis, Archips spp., Argyrotaenia spp., Autographa spp., Busseola fusca, Cadra cautella, Carposina nipponensis, Chilo spp., Choristoneura spp., Clysia ambi-guella, Cnaphalocrocis spp., Cnephasia spp., Cochylis spp., Coleophora spp., Crocidolomia binotalis, Cryptophlebia leucotreta, Cydia spp., Diatraea spp., Diparopsis castanea, Earias spp., Ephestia spp., Eucosma spp., Eupoecilia ambiguella, Euproctis spp., Euxoa spp., Grapholita spp., Hedya nubiferana, Heliothis spp., Hellula undalis, Hyphantria cunea, Keiferia lycopersicella, Leucoptera scitella, Lithocollethis spp., Lobesia botrana, Lymantria spp., Ly-onetia spp., Malacosoma spp., Mamestra brassicae, Manduca sexta, Operophtera spp., Ostrinia nubilalis, Pammene spp., Pandemis spp., Panolis flammea, Pectinophora gossypiela, Phthorimaea operculella, Pieris rapae, Pieris spp., Plutella xylostella, Prays spp., Scirpophaga spp., Sesamia spp., Sparganothis spp., Spodoptera spp., Synanthedon spp., Thaumetopoea spp., Tortrix spp., Trichoplusia ni and Yponomeuta spp.;

from the order Mallophaga, for example,

Damalinea spp. and Trichodectes spp.;

from the order Orthoptera, for example,

Blatta spp., Blattella spp., Gryllotalpa spp., Leucophaea maderae, Locusta spp., Periplaneta spp. and Schistocerca spp.;

from the order Psocoptera, for example,

Lipocelis spp.;

from the order Siphonaptera, for example,

Ceratophyllus spp., Ctenocephalides spp. and Xenopsylla cheopis;

from the order Thysanoptera, for example,

Frankliniella spp., Hercinothrips spp., Scirtothrips aurantii, Taeniothrips spp., Thrips palmi and Thrips tabaci;

from the order Thysanura, for example,

Lepisma saccharina;

nematodes, for example root knot nematodes, stem eelworms and foliar nematodes; especially Heterodera spp., for example Heterodera schachtii, Heterodora avenae and Heterodora trifolii; Globodera spp., for example Globodera rostochiensis; Meloidogyne spp., for example Meloidogyne incoginita and Meloidogyne javanica; Radopholus spp., for example Radopholus similis; Pratylenchus, for example Pratylenchus neglectans and Pratylenchus penetrans; Tylenchulus, for example Tylenchulus semipenetrans; Longidorus, Trichodorus, Xiphinema, Ditylenchus, Aphelenchoides and Anguina; crucifer flea beetles (Phyllotreta spp.);

root maggots (Delia spp.) and cabbage seedpod weevil (Ceutorhynchus spp.).

These compositions according to the invention can be used for controlling, i.e. containing or destroying, animal pests of the above-mentioned type which occur on useful plants in agriculture, in horticulture and in forests, or on organs of useful plants, such as fruits, flowers, foliage, stalks, tubers or roots, and in some cases even on organs of useful plants which are formed at a later point in time remain protected against these animal pests.

In general, the weight ratio of component (A) to component (B), the weight ratio of component (A) to component (C), and the weight ratio of component (B) to component (C) is from 1000:1 to 1:1000.

A non-limiting example for such weight ratios is a composition, wherein the weight ratio of the compound of formula (I): fludioxonil:difenoconazole is 10:1:1. In this example the weight ratio of the compound of formula (I): fludioxonil, i.e. (A:B), is 10:1; the weight ratio of the compound of formula (I): difenoconazole, i.e. (A:C), is 10:1; and the weight ratio of fludioxonil:difenoconazole, i.e. (B:C), is 1:1.

In one embodiment of the invention, component (C) is a fungicide. In this embodiment of the invention, the weight ratio of (A) to (B), of (A) to (C) and of (B) to (C) is preferably from 100:1 to 1:100; more preferably from 20:1 to 1:20; and even more preferably from 10:1 to 1:10.

In another embodiment of the invention, component (C) is an insecticide. In this embodiment of the invention, the weight ratio of (A) to (B), of (A) to (C) and of (B) to (C) is preferably from 400:1 to 1:400. More preferably, in said embodiment of the invention, the weight ratio of (A) to (B) and of (A) to (C) is from 100:1 to 1:100 and the weight ratio of (B) to (C) is from 100:1 to 1:400. Yet more preferably the weight ratio of (A) to (B) is from 20:1 to 1:20; of (A) to (C) is from 20:1 to 1:100 and of (B) to (C) is from 20:1 to 1:400. Yet even more preferably, the weight ratio of (A) to (B) is from 10:1 to 1:10; of (A) to (C) is from 10:1 to 1:80 and of (B) to (C) is from 20:1 to 1:400. In one embodiment of the invention, wherein component (C) is an insecticide, the weight ratio of (A) to (B) is from 10:1 to 1:5; of (A) to (C) is from 1:1 to 1:20 and of (B) to (C) is from 1:1 to 1:100.

It has been found, surprisingly, that certain weight ratios of component (A) to the combination of components (B) and (C) are able to give rise to synergistic activity.

Therefore, a further aspect of the invention are compositions, wherein component (A), component (B) and component (C) are present in the composition in amounts producing a synergistic effect. This synergistic activity is apparent from the fact that the fungicidal activity of the composition comprising component (A), component (B) and component (C) is greater than the sum of the fungicidal activities of component (A) and of the combined components (B) and (C). This synergistic activity extends the range of action of component (A), component (B) and component (C) in two ways. Firstly, the rates of application of component (A), component (B) and component (C) are lowered whilst the action remains equally good, meaning that the active ingredient mixture still achieves a high degree of phytopathogen control even where the three individual components have become totally ineffective in such a low application rate range. Secondly, there is a substantial broadening of the spectrum of phytopathogens that can be controlled.

However, besides the actual synergistic action with respect to fungicidal activity, the compositions according to the invention can also have further surprising advantageous properties. Examples of such advantageous properties that may be mentioned are: more advantageuos degradability; improved toxicological and/or ecotoxicological behaviour; or improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination.

The compositions according to the invention have a systemic action and can be used as foliar, soil and seed treatment fungicides.

With the compositions according to the invention it is possible to inhibit or destroy the phytopathogenic microorganisms which occur in plants or in parts of plants (fruit, blossoms, leaves, stems, tubers, roots) in different useful plants, while at the same time the parts of plants which grow later are also protected from attack by phytopathogenic microorganisms.

The compositions according to the invention can be applied to the phytopathogenic microorganisms, the useful plants, the locus thereof, the propagation material thereof, storage goods or technical materials threatened by microorganism attack.

The compositions according to the invention may be applied before or after infection of the useful plants, the propagation material thereof, storage goods or technical materials by the microorganisms.

The amount of a composition according to the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of fungi to be controlled or the application time.

When applied to the useful plants component (A) is applied at a rate of 5 to 2000 g a.i./ha, particularly 10 to 1000 g a.i./ha, e.g. 50, 75, 100 or 200 g a.i./ha, in association with 1 to 5000 g a.i./ha, particularly 2 to 2000 g a.i./ha, e.g. 100, 250, 500, 800, 1000, 1500 g a.i./ha of component (B) and in association with 1 to 2000 g a.i./ha, particularly 1 to 5000 g a.i./ha, particularly 2 to 2000 g a.i./ha, e.g. 100, 250, 500, 800, 1000, 1500 g a.i./ha of component (C).

In agricultural practice the application rates of the compositions according to the invention depend on the type of effect desired, and typically range from 7 to 12000 g of total composition per hectare, more preferably from 20 to 4000 g of total composition per hectare.

In one embodiment of the invention, component (C) is a fungicide. In this embodiment, when the compositions according to the invention are used for treating seed, rates of 0.5 to 100 g of component (A) per 100 kg of seed, preferably from 2.5 to 40 g per 100 kg of seed, more preferably from 5 to 10 g per 100 kg of seed, and 0.01 to 200 g of component (B) per 100 kg of seed, preferably from 0.1 to 50 g per 100 kg of seed, more preferably from 1 to 20 g per 100 kg of seed, and 0.01 to 200 g of component (C) per 100 kg of seed, preferably from 0.1 to 50 g per 100 kg of seed, more preferably from 1 to 20 g per 100 kg of seed are generally sufficient.

In another embodiment of the invention, component (C) is an insecticide. In this embodiment, when the compositions according to the invention are used for treating seed, components (A) and (B) are typically applied in rates as described above, whereas component (C) is applied at rates of 0.01 to 2000 g per 100 kg of seed, preferably from 0.1 to 1000 g per 100 kg of seed, more preferably from 1 to 400 g per 100 kg of seed.

The composition of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate inert formulation adjuvants (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the compositions according to the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least component (A) together with component (B) together with component (C), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

The Examples which follow serve to illustrate the invention, "active ingredient" denoting a mixture of component (A), component (B) and component (C) in a specific mixing ratio.

FORMULATION EXAMPLES

| Wettable powders | a) | b) | c) |
|---|---|---|---|
| active ingredient [A):B):C) = 1:3:3(a), 1:2:2(b), 1:1:1(c)] | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [A):B):C) = 1:3:3(a), 1:2:2(b), 1:1:1(c)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient (A):B):C) = 1:6:6) | 10% |
| octylphenol polyethylene glycol ether (4-5 mol of ethylene oxide) | 3% |
| calcium dodecylbenzenesulfonate | 3% |
| Castor oil polyglycol ether (35 mol of ethylene oxide) | 4% |
| Cyclohexanone | 30% |
| Xylene mixture | 50% |

Emulsions of any required dilution, which can be used in plant protection, can be obtained from this concentrate by dilution with water.

| Dusts | a) | b) | c) |
|---|---|---|---|
| Active ingredient [A):B):C) = 1:6:6(a), 1:2:2(b), 1:10:10(c)] | 5% | 6% | 4% |
| Talcum | 95% | — | — |
| Kaolin | — | 94% | — |
| Mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient (A):B):C) = 2:1:1) | 15% |
| Sodium lignosulfonate | 2% |
| Carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient (A):B):C) = 1:10:10) | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient (A):B):C) = 1:8:8) | 40% |
| propylene glycol | 10% |
| nonylphenol polyethylene glycol ether (15 mol of ethylene oxide) | 6% |
| Sodium lignosulfonate | 10% |
| Carboxymethylcellulose | 1% |
| Silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient (A):B):C) = 1:8:8) | 40% |
| propylene glycol | 5% |
| copolymer butanol PO/EO | 2% |
| tristyrenephenole with 10-20 moles EO | 2% |

-continued

| Flowable concentrate for seed treatment | |
|---|---|
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula (I), a compound of component (B) and a compound of component (C), or of each of these compounds separately, are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The median capsule diameter is 8-15 microns. The resulting formulation is applied to seeds as an aqueous suspension in an apparatus suitable for that purpose.

Biological Examples

In comparison with a two-component mixture of active ingredients, such as, for example (B+C), the action to be expected (additive action) E for a given active ingredient combination of three components (A+B+C) can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture $X_{BC}$=% action by a mixture (B+C), for example, using p ppm of active ingredient.

Z=% action by active ingredient A) using r ppm of active ingredient.

$$E = X_{BC} + [Z(100-X)/100]$$

Thus, if the observed action for the given combination of three active ingredients (A+B+C) is greater than the action to be expected from the Colby formula, then synergism is present.

The synergistic effect of the compositions of the present invention is demonstrated in the following Examples.

If the action actually observed (O) is greater than the expected action (E), then the action of the combination is super-additive, i.e. there is a synergistic effect. In mathematical terms, synergism corresponds to a positive value for the difference of (O–E). In the case of purely complementary addition of activities (expected activity), said difference (O–E) is zero. A negative value of said difference (O–E) signals a loss of activity compared to the expected activity.

Example B-1

Activity against *Pyrenophora Graminea*

Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is measured photometrically after 72 hrs. The fungicide interactions in the combinations are calculated according to COLBY method.

Compound A as used in examples B-1 to B-5 has been the trans-isomer of the compound of formula I in racemic form.

| Dosage in mg active ingredient/ liter final medium ppm) | | | | | |
|---|---|---|---|---|---|
| Cpd A in ppm | Mixture (Fludioxonil/ Difenoconazole, 1:1) in ppm | Cpd A + Mixture in ppm/ppm | Expected control in % (% $C_{exp}$) | Observed control in % (% $C_{obs}$) | Synergy Factor SF = % $C_{obs}$/% $C_{exp}$ |
| 0.125 | — | — | — | 0 | — |
| 0.0625 | — | — | — | 4.0 | — |
| 0.03125 | — | — | — | 0 | — |
| 0.0039 | — | — | — | 1.3 | — |
| — | 0.0625 | — | — | 70.5 | — |
| — | 0.0156 | — | — | 14.5 | — |
| — | — | 0.0625/0.0156 | 17.9 | 25.6 | 1.4 |
| — | — | 0.125/0.0625 | 70.5 | 90.9 | 1.3 |
| — | — | 0.03125/0.0156 | 14.5 | 21.8 | 1.5 |
| — | — | 0.0625/0.0625 | 71.6 | 85.3 | 1.2 |

-continued

| | | 0.03125/0.0625 | 70.5 | 97.3 | 1.4 |
| | | 0.0039/0.0156 | 15.6 | 19.2 | 1.2 |

Dosage in mg active ingredient/
liter final medium ppm)

| Cpd A in ppm | Mixture (Fludioxonil/ Mefenoxam, 2:1) in ppm | Cpd A + Mixture in ppm/ppm | Expected control in % (% $C_{exp}$) | Observed control in % (% $C_{obs}$) | Synergy Factor SF = % $C_{obs}$/% $C_{exp}$ |
|---|---|---|---|---|---|
| 0.125 | — | — | — | 0 | — |
| 0.03125 | — | — | — | 5.8 | — |
| — | 0.0625 | — | — | 36.9 | — |
| — | 0.0078 | — | — | 0 | — |
| — | — | 0.03125/0.0078 | 5.8 | 15.1 | 2.6 |
| — | — | 0.125/0.0625 | 36.9 | 47.0 | 1.3 |

Dosage in mg active ingredient/
liter final medium ppm)

| Cpd A in ppm | Mixture (Azoxystrobin/ Mefenoxam, 1:1) in ppm | Cpd A + Mixture in ppm/ppm | Expected control in % (% $C_{exp}$) | Observed control in % (% $C_{obs}$) | Synergy Factor SF = % $C_{obs}$/% $C_{exp}$ |
|---|---|---|---|---|---|
| 1.0 | — | — | — | 0 | — |
| 0.0078 | — | — | — | 0 | — |
| 0.002 | — | — | — | 0 | — |
| — | 1.0 | — | — | 83.9 | — |
| — | 0.002 | — | — | 9.1 | — |
| — | — | 0.0078/0.002 | 9.1 | 11.9 | 1.3 |
| — | — | 1.0/1.0 | 83.9 | 97.4 | 1.2 |
| — | — | 0.002/0.002 | 9.1 | 12.6 | 1.4 |

Dosage in mg active ingredient/
liter final medium ppm)

| Cpd A in ppm | Mixture (Difenoconazole/ Mefenoxam, 4:1) in ppm | Cpd A + Mixture in ppm/ppm | Expected control in % (% $C_{exp}$) | Observed control in % (% $C_{obs}$) | Synergy Factor SF = % $C_{obs}$/% $C_{exp}$ |
|---|---|---|---|---|---|
| 0.125 | — | — | — | 0 | — |
| 0.03125 | — | — | — | 0 | — |
| 0.0156 | — | — | — | 0 | — |
| 0.0039 | — | — | — | 3.3 | — |
| — | 0.03125 | — | — | 27.7 | — |
| — | 0.0156 | — | — | 19.6 | — |
| — | 0.0078 | — | — | 0 | — |
| — | — | 0.125/0.03125 | 27.7 | 42.4 | 1.5 |
| — | — | 0.03125/0.03125 | 27.7 | 38.4 | 1.4 |
| — | — | 0.0156/0.0156 | 19.6 | 27.5 | 1.4 |
| — | — | 0.0156/0.03125 | 27.7 | 33.8 | 1.2 |
| — | — | 0.0039/0.0078 | 3.3 | 25.4 | 7.6 |

Example B-2

Activity Against *Gäumannomyces Graminis*

Mycelial fragments of a newly grown culture of the fungus, are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is measured photometrically after 72 hrs. The fungicide interactions in the combinations are calculated according to COLBY method.

| Dosage in mg active ingredient/ liter final medium ppm) | | | | | |
|---|---|---|---|---|---|
| Cpd A in ppm | Mixture (Fludioxonil/ Difenoconazole, 1:1) in ppm | Cpd A + Mixture in ppm/ppm | Expected control in % (% $C_{exp}$) | Observed control in % (% $C_{obs}$) | Synergy Factor SF = % $C_{obs}$/% $C_{exp}$ |
| 1.0 | — | — | — | 19.4 | — |
| 0.5 | — | — | — | 0 | — |
| 0.125 | — | — | — | 0 | — |
| — | 0.5 | — | — | 53.2 | — |
| — | 0.25 | — | — | 26.0 | — |
| — | — | 1.0/0.5 | 62.3 | 72.0 | 1.2 |
| — | — | 0.5/0.25 | 26.0 | 41.2 | 1.6 |
| — | — | 0.125/0.5 | 53.2 | 63.4 | 1.2 |

Example B-3

Activity against *Rhizoctonia Solani*

Mycelial fragments of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is determined photometrically after 48 hrs. The fungicide interactions in the combinations are calculated according to COLBY method.

| Dosage in mg active ingredient/ liter final medium ppm) | | | | | |
|---|---|---|---|---|---|
| Cpd A in ppm | Mixture (Fludioxonil/ Difenoconazole, 1:1) in ppm | Cpd A + Mixture in ppm/ppm | Expected control in % (% $C_{exp}$) | Observed control in % (% $C_{obs}$) | Synergy Factor SF = % $C_{obs}$/% $C_{exp}$ |
| 0.125 | — | — | — | 40.2 | — |
| 0.0625 | — | — | — | 0 | — |
| — | 0.25 | — | — | 13.5 | — |
| — | — | 0.125/0.25 | 48.3 | 60.3 | 1.2 |
| — | — | 0.0625/0.25 | 13.5 | 41.5 | 3.1 |

| Dosage in mg active ingredient/ liter final medium ppm) | | | | | |
|---|---|---|---|---|---|
| Cpd A in ppm | Mixture (Azoxystrobin/ Mefenoxam, 1:1) in ppm | Cpd A + Mixture in ppm/ppm | Expected control in % (% $C_{exp}$) | Observed control in % (% $C_{obs}$) | Synergy Factor SF = % $C_{obs}$/% $C_{exp}$ |
| 0.25 | — | — | — | 73.2 | — |
| 0.125 | — | — | — | 22.8 | — |
| 0.0625 | — | — | — | 0 | — |
| — | 0.5 | — | — | 15.5 | — |
| — | 0.25 | — | — | 18.0 | — |
| — | 0.125 | — | — | 1.3 | — |
| — | 0.0625 | — | — | 0 | — |
| — | — | 0.25/0.0625 | 73.2 | 87.3 | 1.2 |
| — | — | 0.25/0.125 | 73.6 | 92.1 | 1.3 |

-continued

| | | | | | |
|---|---|---|---|---|---|
| — | — | 0.125/0.0625 | 22.8 | 65.6 | 2.9 |
| — | — | 0.25/0.25 | 78.0 | 91.6 | 1.2 |
| — | — | 0.125/0.125 | 23.8 | 77.2 | 3.2 |
| — | — | 0.125/0.25 | 36.6 | 81.7 | 2.2 |
| — | — | 0.0625/0.125 | 1.3 | 23.8 | 18.2 |
| — | — | 0.125/0.5 | 34.7 | 86.4 | 2.6 |
| — | — | 0.0625/0.25 | 18.0 | 58.1 | 3.2 |

| | Dosage in mg active ingredient/ liter final medium ppm) | | | | |
|---|---|---|---|---|---|
| Cpd A in ppm | Mixture (Difenoconazole/ Mefenoxam, 4:1) in ppm | Cpd A + Mixture in ppm/ppm | Expected control in % (% $C_{exp}$) | Observed control in % (% $C_{obs}$) | Synergy Factor SF = % $C_{obs}$/% $C_{exp}$ |
| 0.125 | — | — | — | 23.0 | — |
| — | 0.5 | — | — | 10 | — |
| — | 0.25 | — | — | 0 | — |
| — | 0.125 | — | — | 0 | — |
| — | — | 0.125/0.125 | 23.0 | 26.4 | 1.2 |
| — | — | 0.125/0.25 | 23.0 | 29.6 | 1.3 |
| — | — | 0.125/0.5 | 23.0 | 47.7 | 2.1 |

| | Dosage in mg active ingredient/ liter final medium ppm) | | | | |
|---|---|---|---|---|---|
| Cpd A in ppm | Mixture (Thiabendazole/ Mefenoxam, 9:1) in ppm | Cpd A + Mixture in ppm/ppm | Expected control in % (% $C_{exp}$) | Observed control in % (% $C_{obs}$) | Synergy Factor SF = % $C_{obs}$/% $C_{exp}$ |
| 0.125 | — | — | — | 29.3 | — |
| — | 0.125 | — | — | 0 | — |
| — | 0.0625 | — | — | 4.0 | — |
| — | — | 0.125/0.0625 | 32.2 | 42.8 | 1.3 |
| — | — | 0.125/0.125 | 29.3 | 45.7 | 1.6 |

Example B-4

Activity against *Pythium Ultimum*

Mycelial fragments of a newly grown liquid culture of the fungus are directly mixed into nutrient broth (PDB potato dextrose broth). After placing a (DMSO) solution of the test compounds into a microtiter plate (96-well format) the nutrient broth containing the fungal mycelia/spore mixture is added. The test plates are incubated at 24° C. and the inhibition of growth is determined photometrically after 48 hrs. The fungicide interactions in the combinations are calculated according to COLBY method.

| | Dosage in mg active ingredient/ liter final medium ppm) | | | | |
|---|---|---|---|---|---|
| Cpd A in ppm | Mixture (Azoxystrobin/ Mefenoxam, 1:1) in ppm | Cpd A + Mixture in ppm/ppm | Expected control in % (% $C_{exp}$) | Observed control in % (% $C_{obs}$) | Synergy Factor SF = % $C_{obs}$/% $C_{exp}$ |
| 0.03125 | — | — | — | 0 | — |
| 0.0078 | — | — | — | 0 | — |
| 0.0039 | — | — | — | 0 | — |
| — | 0.0156 | — | — | 22.6 | — |
| — | 0.0078 | — | — | 3.0 | — |
| — | — | 0.03125/0.0156 | 22.6 | 27.0 | 1.2 |
| — | — | 0.0078/0.0078 | 3.0 | 10.6 | 3.5 |
| — | — | 0.0039/0.0156 | 22.6 | 30.0 | 1.3 |

Example B-5

Activity against *Fusarium Graminearum*

Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is determined photometrically after 48 hrs. The fungicide interactions in the combinations are calculated according to COLBY method.

| | Dosage in mg active ingredient/liter final medium ppm) | | | | |
|---|---|---|---|---|---|
| Cpd A in ppm | Mixture (Fludioxonil/ Difenoconazole, 1:1) in ppm | Cpd A + Mixture in ppm/ppm | Expected control in % (% $C_{exp}$) | Observed control in % (% $C_{obs}$) | Synergy Factor SF = % $C_{obs}$/% $C_{exp}$ |
| 1.0 | — | — | — | 5.8 | |
| 0.5 | — | — | — | 9.3 | |
| 0.25 | — | — | — | 10.5 | — |
| 0.125 | — | — | — | 3.5 | — |
| 0.0625 | — | — | — | 2.0 | — |
| 0.03125 | — | — | — | 0 | — |
| — | 0.25 | — | — | 39.9 | — |
| — | 0.125 | — | — | 12.1 | — |
| — | 0.03125 | — | — | 4.5 | — |
| — | — | 1.0/0.25 | 43.4 | 62.2 | 1.4 |
| — | — | 0.125/0.03125 | 7.8 | 13.5 | 1.7 |
| — | — | 0.5/0.25 | 45.5 | 62.8 | 1.4 |
| — | — | 0.25/0.125 | 21.3 | 30.2 | 1.4 |
| — | — | 0.25/0.25 | 46.2 | 65.2 | 1.4 |
| — | — | 0.125/0.125 | 15.2 | 24.5 | 1.6 |
| — | — | 0.0625 7 0.125 | 13.8 | 20.0 | 1.5 |
| — | — | 0.0625/0.25 | 41.1 | 62.6 | 1.5 |
| — | — | 0.03125/0.125 | 12.1 | 15.1 | 1.3 |

| | Dosage in mg active ingredient/liter final medium ppm) | | | | |
|---|---|---|---|---|---|
| Cpd A in ppm | Mixture (Azoxystrobin/ Mefenoxam, 1:1) in ppm | Cpd A + Mixture in ppm/ppm | Expected control in % (% $C_{exp}$) | Observed control in % (% $C_{obs}$) | Synergy Factor SF = % $C_{obs}$/% $C_{exp}$ |
| 1.0 | — | — | — | 6.6 | — |
| 0.25 | — | — | — | 4.0 | — |
| 0.0625 | — | — | — | 4.2 | — |
| — | 1.0 | — | — | 21.8 | — |
| — | 0.125 | — | — | 1.0 | — |
| — | 0.0625 | — | — | 0 | — |
| — | — | 0.25/0.0625 | 4.0 | 10.3 | 2.6 |
| — | — | 0.25/0.125 | 4.9 | 13.3 | 2.7 |
| — | — | 1.0/1.0 | 26.9 | 3.2 | 1.3 |
| — | — | 0.0625/0.125 | 5.2 | 12.4 | 2.4 |
| — | — | 0.25/1.0 | 24.9 | 37.1 | 1.5 |

What is claimed is:

1. A composition suitable for control of diseases caused by phytopathogens comprising
(A) a compound of formula I

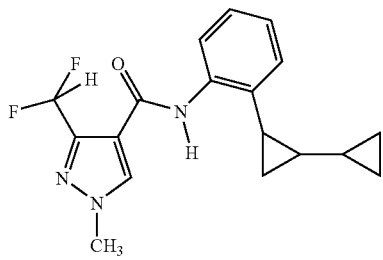

or a tautomer of such a compound;
(B) a fungicide selected from the group consisting of fludioxonil, metalaxyl, mefenoxam, cyprodinil, azoxystrobin, tebuconazole, difenoconazole and thiabendazole; and
(C) a compound selected from the group consisting of an azole fungicide; an anilino-pyrimidine fungicide; a strobilurin fungicide; an acylalanine fungicide; a benzimidazole fungicide; a fungicide selected from the group consisting of silthiofam, furametpyr and penthiopyrad; and an insecticide selected from the group consisting of abamectin, clothianidin, cyromazine, diafenthiuron, diazinon, emamectin benzoate, fenoxycarb, fosthiazate, imidacloprid, lambda-cyhalothrin, lufenuron, methidathion, methiocarb, profenofos, pymetrozine, spinosad, tefluthrin, thiamethoxam, thiodicarb, a compound of formula C-1

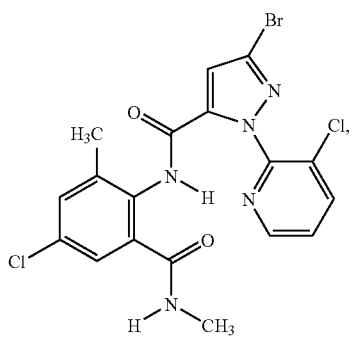

and a compound of formula C-2

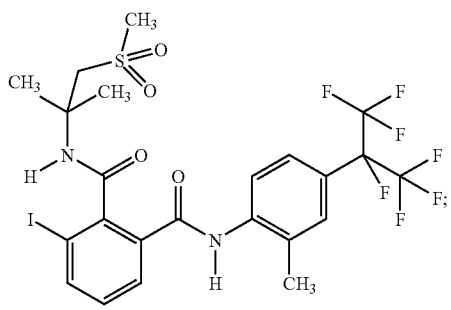

wherein (B) and (C) are different compounds.

2. A composition according to claim 1, wherein (B) is fludioxonil.

3. A composition according to claim 2, wherein (C) is an azole fungicide or an acylalanine fungicide.

4. A composition according to claim 2, wherein (C) is difenoconazole or mefenoxam.

5. A composition according to claim 1, wherein (B) is mefenoxam or metalaxyl.

6. A composition according to claim 1, wherein (B) is mefenoxam.

7. A composition according to claim 6, wherein (C) is an azole fungicide, a strobilurin fungicide or an acylalanine fungicide.

8. A composition according to claim 6, wherein (C) is difenoconazole, azoxystrobin or thiabendazole.

9. A composition according to claim 1, wherein the weight ratio of (A) to (B), the weight ratio of (A) to (C) and the weight ratio of (B) to (C) is from 1000 : 1 to 1 : 1000.

10. A method of controlling diseases on plants or on propagation material thereof caused by phytopathogens, which comprises applying to the plants, the locus thereof or propagation material thereof a composition according to claim 1.

11. A method according to claim 10, which comprises applying to the propagation material of the plants a composition according to claim 1.

12. A method of protecting storage goods, which comprises applying to the storage goods a composition according to claim 1.

13. A composition according to claim 1, wherein (B) is Fludioxonil (C) is Mefenoxam and which composition additionally comprises Thiamethoxam.

14. A composition according to claim 1, wherein (B) is Fludioxonil (C) is Mefenoxam and which composition additionally comprises Thiabendazole.

15. A composition according to claim 1, wherein (B) is Fludioxonil (C) is Mefenoxam and which composition additionally comprises Difenoconazole.

16. A method of controlling diseases on plants or on propagation material thereof caused by phytopathogens, which comprises applying to the plants, the locus thereof or propagation material thereof a composition according to claim 13.

17. A method of controlling diseases on plants or on propagation material thereof caused by phytopathogens, which comprises applying to the plants, the locus thereof or propagation material thereof a composition according to claim 14.

18. A method of controlling diseases on plants or on propagation material thereof caused by phytopathogens, which comprises applying to the plants, the locus thereof or propagation material thereof a composition according to claim 15.

* * * * *